US008709003B2

(12) United States Patent
Island et al.

(10) Patent No.: US 8,709,003 B2
(45) Date of Patent: Apr. 29, 2014

(54) CAPACITIVE SENSING METHOD AND DEVICE FOR DETECTING SKIN

(75) Inventors: Tobin C. Island, Oakland, CA (US); Mark V. Weckwerth, Pleasanton, CA (US); Harvey I. Liu, Fremont, CA (US); Jeffrey A. Hoenshell, Pleasanton, CA (US); Charles A. Schuetz, Oakland, CA (US)

(73) Assignee: Tria Beauty, Inc., Pleasanton, CA (US)

( * ) Notice: Subject to any disclaimer, the term of this patent is extended or adjusted under 35 U.S.C. 154(b) by 1100 days.

(21) Appl. No.: 12/189,079

(22) Filed: Aug. 8, 2008

(65) Prior Publication Data

US 2009/0043294 A1 Feb. 12, 2009

Related U.S. Application Data

(63) Continuation-in-part of application No. 10/783,607, filed on Feb. 19, 2004, now Pat. No. 7,118,563, which is a continuation-in-part of application No. 11/545,963, filed on Oct. 10, 2006, now Pat. No.

(Continued)

(51) Int. Cl.
*A61B 18/18* (2006.01)
(52) U.S. Cl.
USPC .................. 606/9; 607/88; 607/89
(58) Field of Classification Search
USPC .................. 606/9; 607/88–93
See application file for complete search history.

(56) References Cited

U.S. PATENT DOCUMENTS

| 3,307,533 A | 3/1967 | Meredith et al. ............. 601/150 |
| 3,538,919 A | 11/1970 | Meyer ............................ 606/36 |

(Continued)

FOREIGN PATENT DOCUMENTS

| CN | 2442726 U | 8/2001 | ............. A63H 33/00 |
| DE | 19629978 A1 | 1/1998 | ............. F41A 33/02 |

(Continued)

OTHER PUBLICATIONS

European Search Report, Application No. 08797565.2, 6 pages, Oct. 29, 2012.

(Continued)

*Primary Examiner* — Bill Thomson
*Assistant Examiner* — Jeffrey Lipitz
(74) *Attorney, Agent, or Firm* — King & Spalding L.L.P.

(57) ABSTRACT

A skin proximity sensor and method are disclosed in a dermatologic treatment device that includes a bezel or similar surface, and a treatment source capable of being activated to supply a dermatologic treatment through the bezel or surface, such as a window or similar port. A plurality of contacts leading to remotely located capacitors, in some embodiments, or a plurality of capacitive sensors in other embodiments, is positioned in or under the bezel and around the window, and control circuitry coupled to the plurality of capacitors senses the change in capacitance due to skin and inhibits activation of the dermatologic treatment device unless the proximity of skin is sensed. The presence of skin is detected, for example, by measuring changes in charge and discharge times, indicating a variation in capacitance.

12 Claims, 6 Drawing Sheets

Related U.S. Application Data

(63) 8,551,104, which is a continuation of application No. 10/783,607, filed on Feb. 19, 2004, now Pat. No. 7,118,563, application No. 12/189,079, which is a continuation of application No. 10/783,603, filed on Feb. 19, 2004, now Pat. No. 7,452,356, and a continuation of application No. 10/783,880, filed on Feb. 19, 2004, now Pat. No. 7,250,045, and a continuation of application No. 10/787,720, filed on Feb. 25, 2004, now Pat. No. 7,413,567, and a continuation of application No. 10/787,969, filed on Feb. 25, 2004, now Pat. No. 7,981,111, and a continuation of application No. 10/788,167, filed on Feb. 25, 2004, now abandoned, and a continuation of application No. 11/829,747, filed on Jul. 27, 2007, and a continuation of application No. 10/794,504, filed on Mar. 5, 2004, now abandoned.

(60) Provisional application No. 60/954,682, filed on Aug. 8, 2007, provisional application No. 60/450,243, filed on Feb. 25, 2003, provisional application No. 60/450,598, filed on Feb. 26, 2003, provisional application No. 60/451,091, filed on Feb. 28, 2003, provisional application No. 60/452,304, filed on Mar. 4, 2003, provisional application No. 60/451,981, filed on Mar. 4, 2003, provisional application No. 60/452,591, filed on Mar. 6, 2003, provisional application No. 60/456,379, filed on Mar. 20, 2003, provisional application No. 60/456,586, filed on Mar. 21, 2003, provisional application No. 60/458,861, filed on Mar. 27, 2003, provisional application No. 60/472,056, filed on May 20, 2003.

(56) References Cited

U.S. PATENT DOCUMENTS

| | | | | |
|---|---|---|---|---|
| 3,622,743 | A | 11/1971 | Muncheryan | 219/121.63 |
| 3,693,623 | A | 9/1972 | Harte et al. | 606/9 |
| 3,821,510 | A | 6/1974 | Muncheryan | 219/121.79 |
| 3,834,391 | A | 9/1974 | Block | 128/303.1 |
| 4,232,678 | A | 11/1980 | Skovajsa | 607/89 |
| 4,240,738 | A | 12/1980 | Praamsma | |
| 4,354,092 | A | 10/1982 | Manabe et al. | 219/225 |
| 4,388,924 | A | 6/1983 | Weissman et al. | 606/9 |
| 4,423,736 | A | 1/1984 | Dewitt et al. | 600/306 |
| 4,551,628 | A | 11/1985 | Grossman | 250/503.1 |
| 4,573,466 | A | 3/1986 | Simada et al. | 606/11 |
| 4,592,353 | A | 6/1986 | Daikuzono | 606/16 |
| 4,608,978 | A | 9/1986 | Rohr | 606/9 |
| 4,617,926 | A | 10/1986 | Sutton | 606/9 |
| 4,690,141 | A | 9/1987 | Castel et al. | 607/90 |
| 4,733,660 | A | 3/1988 | Itzkan | 606/9 |
| 4,829,262 | A | 5/1989 | Furumoto | 359/346 |
| 4,846,184 | A | 7/1989 | Comment et al. | 600/306 |
| 4,905,690 | A | 3/1990 | Ohshiro et al. | 607/89 |
| 4,930,504 | A | 6/1990 | Diamantopoulos et al. | 607/88 |
| 5,057,104 | A | 10/1991 | Chess | 606/9 |
| 5,059,013 | A | 10/1991 | Jain | 359/503 |
| 5,059,192 | A | 10/1991 | Zaias | 606/9 |
| 5,075,971 | A | 12/1991 | Mccambridge | 30/133 |
| 5,109,465 | A | 4/1992 | Klopotek | 385/133 |
| 5,226,907 | A | 7/1993 | Tankovich | 606/133 |
| 5,259,380 | A | 11/1993 | Mendes et al. | 607/115 |
| 5,282,797 | A | 2/1994 | Chess | 606/9 |
| 5,295,052 | A | 3/1994 | Chin et al. | |
| 5,344,418 | A | 9/1994 | Ghaffari | 606/9 |
| 5,360,426 | A | 11/1994 | Muller et al. | 606/13 |
| 5,401,270 | A | 3/1995 | Muller et al. | 606/13 |
| 5,405,368 | A | 4/1995 | Eckhouse | 607/88 |
| 5,425,728 | A | 6/1995 | Tankovich | 606/9 |
| 5,431,647 | A | 7/1995 | Purcell, Jr. et al. | 606/16 |
| 5,464,434 | A | 11/1995 | Alt | 607/6 |
| 5,464,436 | A | 11/1995 | Smith | 607/89 |
| 5,473,408 | A | 12/1995 | Hoffman et al. | 355/53 |
| 5,486,172 | A | 1/1996 | Chess | 606/20 |
| 5,519,534 | A | 5/1996 | Smith et al. | 359/599 |
| 5,549,660 | A | 8/1996 | Mendes et al. | 607/88 |
| 5,556,612 | A | 9/1996 | Anderson et al. | 424/59 |
| 5,595,568 | A | 1/1997 | Anderson et al. | 606/9 |
| 5,606,798 | A | 3/1997 | Kelman | 30/41.5 |
| 5,624,435 | A | 4/1997 | Furumoto et al. | 606/10 |
| 5,628,744 | A | 5/1997 | Coleman et al. | 606/12 |
| 5,630,811 | A | 5/1997 | Miller | 606/9 |
| 5,632,741 | A | 5/1997 | Zavislan et al. | 606/9 |
| 5,643,252 | A | 7/1997 | Waner et al. | 606/9 |
| 5,647,866 | A | 7/1997 | Zaiase et al. | 606/9 |
| 5,658,323 | A | 8/1997 | Miller | 607/89 |
| 5,669,916 | A | 9/1997 | Anderson | 606/133 |
| 5,683,380 | A | 11/1997 | Eckhouse et al. | 606/9 |
| 5,700,240 | A | 12/1997 | Barwick, Jr. et al. | 604/22 |
| 5,707,403 | A | 1/1998 | Grove et al. | 607/89 |
| 5,728,090 | A | 3/1998 | Martin et al. | 606/3 |
| 5,735,844 | A | 4/1998 | Anderson et al. | 606/9 |
| 5,743,901 | A | 4/1998 | Grove et al. | 606/9 |
| 5,752,948 | A | 5/1998 | Tankovich et al. | 606/9 |
| 5,752,949 | A | 5/1998 | Tankovich et al. | 606/9 |
| 5,766,214 | A | 6/1998 | Mehl, Sr. et al. | 606/9 |
| 5,769,844 | A | 6/1998 | Ghaffari | 606/16 |
| 5,817,089 | A | 10/1998 | Tankovich et al. | 606/9 |
| 5,820,625 | A | 10/1998 | Izawa et al. | 606/9 |
| 5,824,023 | A | 10/1998 | Anderson | 607/88 |
| 5,843,072 | A | 12/1998 | Furumoto et al. | 606/9 |
| 5,846,252 | A | 12/1998 | Mehl, Sr. | 606/133 |
| 5,849,029 | A | 12/1998 | Eckhouse et al. | 607/104 |
| 5,853,407 | A | 12/1998 | Miller | 606/9 |
| 5,868,732 | A | 2/1999 | Waldman et al. | 606/9 |
| 5,871,479 | A | 2/1999 | Furumoto et al. | 606/9 |
| 5,871,480 | A | 2/1999 | Tankovich | 606/9 |
| 5,871,521 | A | 2/1999 | Kaneda et al. | 607/89 |
| 5,879,346 | A | 3/1999 | Waldman et al. | 606/9 |
| 5,885,273 | A | 3/1999 | Eckhouse et al. | 606/9 |
| 5,966,210 | A | 10/1999 | Rosow et al. | 356/213 |
| 5,968,034 | A | 10/1999 | Fullmer et al. | 606/9 |
| 5,989,267 | A | 11/1999 | Anderson | 606/133 |
| 6,015,404 | A | 1/2000 | Altshuler et al. | 606/9 |
| RE36,634 | E | 3/2000 | Ghaffari | 606/9 |
| 6,059,765 | A | 5/2000 | Cole et al. | 604/500 |
| 6,080,146 | A | 6/2000 | Altshuler et al. | 606/9 |
| 6,096,029 | A | 8/2000 | O'Donnell, Jr. | 606/9 |
| 6,106,514 | A | 8/2000 | O'Donnell, Jr. | 606/9 |
| 6,114,862 | A * | 9/2000 | Tartagni et al. | 324/662 |
| 6,138,041 | A | 10/2000 | Yahia | 455/569.2 |
| 6,160,831 | A | 12/2000 | Kleinschmidt et al. | 372/57 |
| 6,183,500 | B1 | 2/2001 | Kohler | 607/88 |
| 6,183,773 | B1 | 2/2001 | Anderson | 424/450 |
| 6,188,495 | B1 | 2/2001 | Inoue et al. | 398/139 |
| 6,197,020 | B1 | 3/2001 | O'donnell, Jr. | 606/9 |
| 6,208,749 | B1 | 3/2001 | Gutkowicz-krusin et al. | 382/128 |
| 6,228,074 | B1 | 5/2001 | Almeida | 606/9 |
| 6,251,127 | B1 | 6/2001 | Biel | 607/88 |
| 6,269,818 | B1 | 8/2001 | Lui et al. | 128/898 |
| 6,273,884 | B1 | 8/2001 | Altshuler et al. | 606/9 |
| 6,273,885 | B1 | 8/2001 | Koop et al. | 606/9 |
| 6,277,111 | B1 | 8/2001 | Clement et al. | 606/9 |
| 6,280,438 | B1 | 8/2001 | Eckhouse et al. | 606/9 |
| 6,290,713 | B1 | 9/2001 | Russell | 607/88 |
| 6,322,584 | B2 | 11/2001 | Ingle et al. | 607/96 |
| 6,379,376 | B1 | 4/2002 | Lubart | 607/88 |
| 6,436,127 | B1 | 8/2002 | Anderson et al. | 607/89 |
| 6,440,122 | B1 | 8/2002 | Shimoji | 606/2 |
| 6,441,943 | B1 | 8/2002 | Roberts et al. | 359/267 |
| 6,485,484 | B1 | 11/2002 | Connors et al. | 606/9 |
| 6,494,900 | B1 | 12/2002 | Salansky et al. | 607/89 |
| 6,508,813 | B1 | 1/2003 | Alshuler | 606/9 |
| 6,511,475 | B1 | 1/2003 | Altshuler et al. | 606/9 |
| 6,514,242 | B1 | 2/2003 | Vasily et al. | 606/9 |
| 6,516,013 | B1 | 2/2003 | Patzel et al. | 372/29.02 |
| 6,517,532 | B1 | 2/2003 | Altshuler et al. | 606/9 |
| 6,533,775 | B1 | 3/2003 | Rizoiu | 606/9 |

(56) References Cited

U.S. PATENT DOCUMENTS

| | | | |
|---|---|---|---|
| 6,536,914 B2 | 3/2003 | Hoelen et al. | |
| 6,548,781 B1 | 4/2003 | Brunwinkel | 219/121.73 |
| 6,563,853 B2 | 5/2003 | Heist et al. | 372/57 |
| 6,600,951 B1 | 7/2003 | Anderson | 604/20 |
| 6,605,080 B1 | 8/2003 | Altshuler et al. | 606/3 |
| 6,610,052 B2 | 8/2003 | Furumoto | 606/9 |
| 6,621,702 B2 | 9/2003 | Elias et al. | 361/700 |
| 6,641,044 B2 | 11/2003 | Plesko | 235/462.49 |
| 6,648,904 B2 | 11/2003 | Altshuler et al. | 607/96 |
| 6,653,618 B2 | 11/2003 | Zenzie | 250/221 |
| 6,659,999 B1 | 12/2003 | Anderson et al. | 606/9 |
| 6,660,000 B2 | 12/2003 | Neuberger et al. | 606/9 |
| 6,663,620 B2 | 12/2003 | Altshuler et al. | 606/9 |
| 6,663,659 B2 | 12/2003 | Mcdaniel | 607/88 |
| 6,666,856 B2 | 12/2003 | Connors et al. | 606/9 |
| 6,723,090 B2 | 4/2004 | Altshuler et al. | 606/9 |
| 6,887,260 B1 | 5/2005 | Mcdaniel | 607/88 |
| 6,902,563 B2 | 6/2005 | Wilkens et al. | 606/9 |
| 7,068,910 B2 | 6/2006 | Duine et al. | |
| 7,452,356 B2 | 11/2008 | Grove et al. | 606/9 |
| 2001/0023363 A1 | 9/2001 | Harth et al. | 607/90 |
| 2001/0046131 A1 | 11/2001 | Hoelen et al. | |
| 2002/0005475 A1 | 1/2002 | Zenzie | 250/221 |
| 2002/0015430 A1 | 2/2002 | Osmanow et al. | 372/55 |
| 2002/0031160 A1 | 3/2002 | Desor | 372/57 |
| 2002/0049483 A1 | 4/2002 | Knowlton | 607/101 |
| 2002/0091377 A1 | 7/2002 | Anderson et al. | 606/9 |
| 2002/0097587 A1 | 7/2002 | Krietzman et al. | 362/553 |
| 2002/0128635 A1 | 9/2002 | Altshuler et al. | 606/9 |
| 2002/0128695 A1 | 9/2002 | Harth et al. | 607/88 |
| 2002/0151887 A1 | 10/2002 | Stern et al. | 606/41 |
| 2002/0161357 A1 | 10/2002 | Anderson et al. | 606/9 |
| 2002/0161418 A1 | 10/2002 | Wilkens et al. | 607/90 |
| 2002/0173780 A1 | 11/2002 | Altshuler et al. | 606/9 |
| 2002/0173833 A1 | 11/2002 | Korman et al. | 607/88 |
| 2002/0183811 A1 | 12/2002 | Irwin | 607/94 |
| 2003/0004499 A1 | 1/2003 | Mcdaniel | 606/3 |
| 2003/0009158 A1 | 1/2003 | Perricone | 606/9 |
| 2003/0032950 A1 | 2/2003 | Altshuler et al. | 606/9 |
| 2003/0036751 A1 | 2/2003 | Anderson et al. | 606/9 |
| 2003/0046825 A1 | 3/2003 | Slingo | 34/96 |
| 2003/0050561 A1 | 3/2003 | Bazin et al. | 600/476 |
| 2003/0055413 A1 | 3/2003 | Altshuler et al. | 606/9 |
| 2003/0055414 A1 | 3/2003 | Altshuler et al. | 606/9 |
| 2003/0065314 A1 | 4/2003 | Altshuler et al. | 606/9 |
| 2003/0080755 A1 | 5/2003 | Kobayashi | |
| 2003/0094714 A1 | 5/2003 | Buazza et al. | 264/1.38 |
| 2003/0105069 A1 | 6/2003 | Robinson et al. | 514/185 |
| 2003/0133292 A1 | 7/2003 | Mueller et al. | 362/231 |
| 2003/0138249 A1 | 7/2003 | Merola et al. | 396/661 |
| 2003/0146122 A1 | 8/2003 | Westfield et al. | 206/349 |
| 2003/0169400 A1 | 9/2003 | Buazza et al. | 351/159.62 |
| 2003/0177657 A1 | 9/2003 | Andis et al. | 34/96 |
| 2003/0195494 A1 | 10/2003 | Altshuler et al. | 606/9 |
| 2003/0199859 A1 | 10/2003 | Altshuler et al. | 606/9 |
| 2003/0216795 A1 | 11/2003 | Harth et al. | 607/88 |
| 2003/0220633 A1 | 11/2003 | Angeley et al. | 606/18 |
| 2003/0233138 A1 | 12/2003 | Spooner | 607/93 |
| 2004/0006328 A1 | 1/2004 | Anderson | 604/501 |
| 2004/0010298 A1 | 1/2004 | Altshuler et al. | 607/88 |
| 2004/0010299 A1 | 1/2004 | Tolkoff et al. | 607/88 |
| 2004/0034319 A1 | 2/2004 | Anderson et al. | 604/20 |
| 2004/0034341 A1 | 2/2004 | Altshuler et al. | 606/3 |
| 2004/0036975 A1 | 2/2004 | Slatkine | 359/584 |
| 2004/0073079 A1 | 4/2004 | Altshuler et al. | 600/1 |
| 2004/0093042 A1 | 5/2004 | Altshuler et al. | 607/88 |
| 2004/0116913 A1 | 6/2004 | Pilcher et al. | 606/9 |
| 2004/0120151 A1 | 6/2004 | Ostler et al. | |
| 2004/0122492 A1 | 6/2004 | Harth et al. | 607/88 |
| 2004/0167499 A1 | 8/2004 | Grove et al. | 606/9 |
| 2004/0167500 A1 | 8/2004 | Weckwerth et al. | 606/9 |
| 2004/0167501 A1 | 8/2004 | Island et al. | 606/9 |
| 2004/0167502 A1 | 8/2004 | Weckwerth et al. | 606/9 |
| 2004/0167592 A1 | 8/2004 | Grove et al. | 607/96 |
| 2004/0176754 A1* | 9/2004 | Island et al. | 606/9 |
| 2004/0176823 A1 | 9/2004 | Island et al. | 607/88 |
| 2004/0225339 A1 | 11/2004 | Yaroslavsky et al. | 607/88 |
| 2005/0085878 A1 | 4/2005 | Wilkens et al. | 607/94 |
| 2005/0276072 A1 | 12/2005 | Hayashi et al. | |
| 2006/0206103 A1 | 9/2006 | Altshuler et al. | |
| 2007/0025947 A1 | 2/2007 | Hansenne et al. | 424/70.22 |
| 2007/0129711 A1 | 6/2007 | Altshuler et al. | |
| 2007/0292461 A1 | 12/2007 | Tamarkin et al. | 424/401 |
| 2008/0125834 A1 | 5/2008 | Hendrix et al. | 607/88 |
| 2008/0147053 A1 | 6/2008 | Kang et al. | 606/9 |

FOREIGN PATENT DOCUMENTS

| | | | | |
|---|---|---|---|---|
| DE | 10044662 A1 | 3/2002 | | A61K 31/60 |
| DE | 10360503 A1 | 7/2005 | | A61K 8/06 |
| EP | 0761257 A2 | 3/1997 | | A61B 18/20 |
| EP | 0933096 A2 | 8/1999 | | A61B 17/00 |
| EP | 1116476 A2 | 7/2001 | | A61B 18/20 |
| EP | 1168535 A1 | 1/2002 | | H01S 5/022 |
| EP | 1358872 A1 | 11/2003 | | A61K 31/192 |
| FR | 2665366 A1 | 2/1992 | | A61N 1/32 |
| FR | 2932679 A1 | 12/2009 | | A61K 8/36 |
| JP | 11244295 A | 9/1999 | | A61B 18/20 |
| JP | 2000300683 A | 10/2000 | | A61B 18/20 |
| JP | 2001252363 A | 9/2001 | | A61B 17/00 |
| JP | 2004527330 A | 9/2004 | | A61B 17/00 |
| JP | 2006518614 A | 8/2006 | | A61B 18/20 |
| JP | 2006525036 A | 11/2006 | | A61B 17/00 |
| WO | 96/14083 A1 | 5/1996 | | A23L 1/015 |
| WO | 00/02491 A1 | 1/2000 | | A61K 41/00 |
| WO | 02/094116 A1 | 11/2002 | | A61B 18/18 |
| WO | 03/017824 A2 | 3/2003 | | A61B 18/00 |
| WO | 03/049633 A1 | 6/2003 | | A45D 26/00 |
| WO | 2004/075731 A2 | 9/2004 | | A61B 18/20 |
| WO | 2004/080279 A2 | 9/2004 | | A61B 18/20 |
| WO | 2005/063193 A1 | 7/2005 | | A61K 8/06 |
| WO | 2009/089177 A1 | 7/2009 | | A61N 1/00 |

OTHER PUBLICATIONS

Brunsting, L, et al., "The Color of the Skin as Analyzed by Spectrophotometric Methods, II. The Role of Pigmentation", Section on Dermatology and Syphilology and the Division of Physics and Biophysical Research, The Mayo Foundation; pp. 575-592, Apr. 29, 1929.

Brunsting, L, et al., The Color of the Skin as Analyzed by Spectrophotometric Methods, III. The Role of Superficial Blook, Section on Dermatology and Syphilology and the Division of Physics and Biophysical Research, The Mayo Foundation; pp. 593-613, Apr. 29, 1929.

Miller, Steve et al., "Isolation and Characterization of Protoporphyrin IX from Bacterial Catalase," The Journal of Biological Chemistry, vol. 235, No. 11, 3 pages, Mar. 7, 1960.

Brown, E.B., "Modern Optics," Radiometry and Photometry, Reinhold Publishing Corporation, 3 pages, 1965.

Cornelius, C.E. et al., "Red Fluorescence of Comedones: Production of Porphyrins by *Corynebacterium acnes*," The Journal of Investigative Dermatology, vol. 49(4), PMID: 4228644, [PubMed—Indexed for Medline], 3 pages, Oct. 1967.

Dalton, J. et al., "Reaction Between Molecular Oxygen and Photoexcited Protoporphyrin IX," Nature, vol. 235, 1 page, Feb. 18, 1972.

Hoeffler, Ulrich, "Enzymatic and Hemolytic Properties of *Propionibacterium acnes* and Related Bacteria," Journal of Clinical Microbiology, vol. 6, No. 6, 4 pages, Jun. 10, 1977.

Formanek, I. et al., "Porphyrinsynthesis by *Propionibacterium acnes* (author's translation)," Archives for Dermatological Research, vol. 259(2), German, PMID: 334087 [PubMed—indexed for Medline], 9 pages, Aug. 22, 1977.

Lee, W.L. et al., "Comparative Studies of Porphyrin Production in *Propionibacterium acnes* and *Propionibaceterium granulosum*," Journal of Bacteriology, vol. 133(2), PMID: 637914 [PubMed—Indexed for Medline] 5 pages, Aug. 25, 1977.

Mills, O.H. et al., "Ultraviolet Phototherapy and Photochemotherapy of *Acne vulgaris*," Archives of Dermatological Research, , vol. 114(2), PMID: 147054 [PubMed: Indexed for Medline] 3 pages, Feb. 1978.

(56) References Cited

OTHER PUBLICATIONS

Fanta, D. et al., "Porphyrinsynthesis of *Propionibacterium acnes* in *Acne* and *Seborrhea* (author's translation)," Archives of Dermatological Research, vol. 261, German, PMID: 148872 [PubMed—indexed for Medline], 5 pages, Apr. 7, 1978.

McGinley, K.J. et al., "Facial Follicular Porphyrin Fluorescence: Correlation with Age and Density of *Propionibacterium acnes*," British Journal of Dermatology, Vo. 102(4), PMID: 7387886 [PubMed—Indexed for Medline] 5 pages, Jul. 24, 1979.

Sliney, D. et al., "Safety with Lasers and Other Optical Sources, A Comprehensive Handbook," Plenum Press, 9 pages, Jul. 1980.

Fanta, D. et al., "Porphyrin Synthesis by *Propionibacteria* in Dependence of External Factors," Archives of Dermatological Research, vol. 271, 7 pages, Jul. 10, 1980.

Melo, T.B. et al., "In Vivo Porphyrin Fluorescence for *Propionibacterium acnes*. A Characterization fo the Fluorescing Pigments," Dermatologica, vol. 164(3), PMID: 7084539 [PubMed—Indexed for Medline] 9 pages, Mar. 1982.

Parrish, J. et al., "Erythema and Melanogenesis Action Spectra of Normal Human Skin," Photochemistry and Photobiology, vol. 36, 5 pages, Mar. 15, 1982.

Kjeldstad, B. et al., "Influence of pH on Porphyrin Production in *Propionibacterium acnes*," Archives of Dermatological Research, vol. 276(6), PMID: 6517611 [PubMed—Indexed for Medline] 5 pages, 1984.

Melo, T.B. et al., "Photodestruction of *Propionibacterium acnes* Porphyrins," Z. Naturforsch, vol. 40(C), PMID: 3993179 [PubMed—Indexed for Medline] 4 pages, Oct. 22, 1984.

Kjeldstad, B. et al., "Porphyrin Photosensitization of Bacteria," Adv. Exp. Med. Biol., PMID: 4096295 [PubMed—indexed for Medline], 5 pages, 1985.

Kjeldstad, B. et al., "An Action Spectrum for Blue and Near Ultraviolet Inactivation of *Propionibacterium acnes*; with Emphasis on a Possible Porphyrin Photosensitization," Photochemistry and Photobiology, vol. 43(1), PMID: 3952162 [PubMed—Indexed for Medline] 4 pages, Jul. 19, 1985.

Guideline for Limits of Exposure to Ultraviolet Radiation of Wavelengths between 180 nm and 400 nm, Health Physics, vol. 49, No. 2, 10 pages, Aug. 1985.

Meffert, H. et al., "Phototherapy of *Acne vulgaris* with the "TuR" UV 10 Body Section Irradiation Unit [translation]," Dermatol. Monatsscher., vol. 172, German, PMID: 2938991 [PubMed—Indexed for Medline] 6 pages, 1986.

Meffert, H. et al., "Phototherapy of *Acne vulgaris* with the UVA Irradiation Instrument TBG 400 [translation]," Dermatol. Monatsscher, vol. 172, German, PMID: 2937663 [PubMed—Indexed for Medline] 2 pages, 1986.

Johnsson, A. et al., "Fluorescence from *Pilosebaceous* Follicles," Archives of Dermatological Research, vol. 279(3), PMID: 3592747 [PubMed—Indexed for Medline] 4 pages, 1987.

Meffert, H. et al., "Treatment of *Acne vulgaris* with Visible Light [translation]," Dermatol. Monatsscher, vol. 173, German, PMID: 2963772 [PubMed—Indexed for Medline] 2 pages, 1987.

Meffert, H. et al., "Verkuzung der Bestrahlungszeit Verwendung eines Hochruckstrahlers vom Blaulichttyp," Dermatol. Mon. schr 176, 8 pages, 1990.

Meffert, H. et al., "Therapy of *Acne* with Visible Light. Decreased Irradiation Time by Using a Blue-Light High-Energy Lamp [translation]" Dermatol. Monatsschr., German, PMID: 2150382 [PubMed—Indexed for Medline] 7 pages, 1990.

Kjeldstad, B. et al., "Near-UV-Induced Radicals in *Propionibacterium acnes*, Studied by Electron Spin Resonance Spectrometry at 77 K.," Journal of Photochemistry and Photobiology, vol. 9(2), PMID: 1650821 [PubMed—Indexed for Medline] 7 pages, Sep. 21, 1990.

Morys et al., "The Accurate Measurements of Biologically Effective Ultraviolet Radiation," International Symposium on High Latitude Optics, 10 pages, Jul. 1993.

Webster, G.F., "Inflammation in *Acne vulgaris*," Journal of the American Academy of Dermatology, vol. 33(2 Pt. 1), Review, PMID: 7622652 [PubMed—Indexed for Medline] 7 pages, Aug. 1995.

Leung, S., "The Porphyrin Page," website at http://www.washburn.edu-cas-chemistry-sleung-porphyrin/page.html, Created Apr. 16, 1996, Last Modified Nov. 11, 2002, printed Jun. 22, 2004, 7 pages, Apr. 16, 1996.

Arakane, K. et al., "Singlet Oxygen (1 delta g) Generation from *Coproporphyrin* in *Propionibacterium acnes* on Irradiation," Biochemical and Biophysical Research Communication, vol. 223, Article No. 0937, PMID: 8687438 [PubMed—Indexed for Medline], 6 pages, Jun. 25, 1996.

Sigurdsson, V. et al., "Phototherapy of *Acne vulgaris* with Visible Light," Dermatology, vol. 194(3), PMID: 9187844 [PubMed—Indexed for Medline] 5 pages, Nov. 15, 1996.

Predicate Devices: LightSheer Diode Laser System by Star Medical/Coherent Star, K973324, K982940, K001746, 1997.

Leyden, J., "Therapy for *Acne vulgaris*," The New England Journal of Medicine, vol. 336, No. 16, Massachussetts Medical Society, 7 pages, Apr. 17, 1997.

Leydon, J., "Therapy for *Acne vulgaris*," The New England Journal of Medicine, Review Article, 6 pages, Apr. 17, 1997.

UV Index definition, Canadian Environmental Web page, See entire document, 3 pages, Jun. 1, 1998.

Karu, Tiina, "Primary and Secondary Mechanisms of Action of Visible to Near-IR Radiation on Cells," Journal of Photochemistry and Photobiology, vol. 49, 17 pages, Nov. 9, 1998.

Saiki, Hiroyasu et al., "Diffusion of Porphyrins and Quinones in Organic Solvents," Phys. Chem. Chem Phys., vol. 1, 4 pages, 1999.

Code of Federal Regulations, Class I Accessible Emmission Limits for Laser Radiation, Food and Drug Administration, HHS, 2 pages, Apr. 1, 1999.

Yoo, Yeong-Min et al., "Hemoglobin Toxicity in Experimental Bacterial Peritonitis Is Due to Production of Reactive Oxygen Species," Clinical and Diagnostic Laboratory Immunology, vol. 6, No. 6, 2 pages, Jul. 12, 1999.

IEC Technical Report 60825-8, "Safety of Laser Products—Guide for the Safe Use of Medical Laser Equipment," 6 pages, Nov. 1999.

Papagcorgiou, P. et al., "Phototherapy wit Blue (415 nm) and Red (660 nm) Light in the Treatment of *Acne vulgaris*," British Journal of Dermatology, vol. 142(5), PMID: 10809858 [PubMed—indexed for Medline] 6 pages, Dec. 7, 1999.

Angelopoulou, E., "The Reflectance Spectrum of Human Skin", Dept. of Computer & Information Science, Technical Reports (CIS), University of Pennsylvania; 14 pages, Dec. 20, 1999.

Romiti, R. et al., "High-Performance Liquid Chromatography Analysis of Porphyrins in *Propionibacterium acnes*," Archives of Dermatological Research, vol. 292(6), PMID: 10929774 [PubMed—Indexed for Medline] 3 pages, Jan. 7, 2000.

Bagdonas, Saulius et al., "Phototransformations of 5-Aminolevulinic Acid-Induced Protoporphyrin IX in Vitro: A Spectroscopic Study," Photochemistry and Photobiology, vol. 72(2), 7 pages, May 6, 2000.

Shalita, A. et al., "*Acne* Photoclearing (APC) Using a Novel, High-Intensity, Enhanced, Narrow-Band, Blue Light Source," Clinical Application Notes, vol. 9(1), ESC Medical Systems Ltd., PB 558-0230, Rev. A, 4 pages, 2001.

International Standard IEC 60825.1, Safety of Laser Products—Part 1: Equipment Classification, Requirements and User's Guide, Editon 1.2, 121 pages, 2001.

Koval'skaya, N.E. et al., "The Efficiency of the Formation of Singlet. Oxygen by a Sensitizer Based on Zinc Phthlocyanine," Journal of Applied Spectroscopy, vol. 68, No. 2, 4 pages, 2001.

Buchezyk, Darius P. et al., "High Efficiency of 5-Aminolevulinate-Photodynamic Treatment Using UVA Irradiation," Carcinogenesis, vol. 22, No. 6, 5 pages, 2001.

Mason, Maria G. et al., "Extracellular Heme Peroxidases in Actinomycetes: a Case of Mistaken Identity," Applied and Environmental Microbiology, vol. 67, No. 10, 8 pages, Jul. 18, 2001.

Jappe, U. et al., "*Propionibacterium acnes* and Inflammation in *Acne; P. acnes* has T-Cell Mitogenic Activity," British Journal of Dermatology, vol. 146, 8 pages, Sep. 12, 2001.

Kawada, A. et al., "*Acne* Phototherapy with a High-Intensity, Enhanced, Narrow-Band, Blue Light Source: An Open Study and In

(56) References Cited

OTHER PUBLICATIONS

Vitro Investigation," Journal of Dermatological Science, vol. 30(2), PMID: 12413768 [PubMed—indexed for Medline] 7 pages, Jun. 19, 2002.
Ashkenazi, H. et al., "Eradication of *Propionibacterium acnes* by its Endogenic Porphyrins after Illumination with High Intensity Blue Light," FEMS Immunology and Medical Microbiology, vol. 35(1), PMID: 12589953 [PubMed: Indexed for MedLine], 8 pages, Jul. 24, 2002.
Harnessing Light to Treat Stretch Marks and Other Hypopigmented Scars, Skin & Aging, Supplement to Nov. 2002 Skin & Aging.
Elman et al., "The Effective Treatment of *Acne vulgaris* by a High-Intensity, Narrow Band 405-420 nm Light Source," Journal of Cosmetic & Laser Therapy, vol. 5, 6 pages, Nov. 27, 2002.
Hode, L., "Are Lasers More Dangerous than IPL Instruments?," Lasers in Surgery and Medicine, Supplement 15, 3 pages, 2003.
Wagener, Frank et al., "Different Faces of the Heme-Heme Oxygenase System in Inflammation," Pharmaceutical Reviews, vol. 55, No. 3, The American Society for Pharmacology and Experimental Therapeutics, 21 pages, 2003.
Anonymous, "Akne-Guidelines Schweiz," [Online], Martin Pletscher: Dermatologie, Retrieved from Internet: http://www.martinpletscher.ch/dermatologie/akne.html, 5 pages, May 15, 2003.
Burkhart, Craig N. et al., "Assessment of Etiologic Agents in *Acne* Pathogenesis," Review, Department of Microbiology and Immunology, and Dermatology, Medical College of Ohio at Toledo, 7 pages, Jul. 2003.
Micro Touch Trimmer website, www.asseenontvwork.com/vcc/ideavillage/microtouch/104917, printed Dec. 4, 2003, 21 pages.
Charakida, A. et al., "Phototherapy in the Treatment of *Acne vulgaris*," American Journal of Clinical Dermatology, vol. 5(4), Adis. Data Information, 6 pages, 2004.
Elman, M. et al., "Light Therapy in the Treatment of *Acne vulgaris*," Dermatological Surgery, vol. 30(2), Dermatology and Lasers Clinic, Tel Aviv and Caesarea, Israel, American Society for Dermatology Surgery, 8 pages, Feb. 2004.
U.S. Appl. No. 10/794,676, by Mark V. Weckworth et al. entitled "Method and Apparatus for the Repigmentation of Human Skin", Mar. 3, 2004.
Elman, M. et al., "The Role of Pulsed Light and Hear Energy (LHE) in *Acne* Clearance," Journal of Cosmetic Laser Therapy, vol. 6, 5 pages, Apr. 1, 2004.
Omi, Tokuya et al., "420 nm Intense Continuous Light Therapy for *Acne*," Journal of Cosmetic Laser Therapy, vol. 6, 7 pages, Aug. 12, 2004.
Krautheim, A. et al., "*Acne*: Topical Treatment," Clinics in Dermatology, vol. 22, No. 5, XP004647111, 10 pages, Sep. 1, 2004.
Ross, Victor E., "Optical Treatment for *Acne*," Deli iatologic Therapy, vol. 18, ISSN 1396-0296, 14 pages, 2005.
Ross, Victor E., "*Acne*, Lasers, and Light," Advances in Dermatology, vol. 21, 29 pages, 2005.
Ortiz, Arisa et al., "A Review of Lasers and Light. Sources in the Treatment of *Acne vulgaris*," Journal of Cosmetic and Laser Therapy, vol. 7, 7 pages, Mar. 7, 2005.

Hamblin, M. et al., "*Helicobacter phylori* Accumulates Photoactive Porphyrins and Is Killed by Visible Light," Antimicrobial Agents and Chemotherapy, vol. 49, No. 7, American Society for Microbiology, 6 pages, Mar. 7, 2005.
Mariwalla, Kavita et al., "Use of Lasers and Light-Based Therapies for Treatment of *Acne vulgaris*," Lasers in Surgery and Medicine, vol. 37, 10 pages, Oct. 12, 2005.
Mariwalla, Kavita et al., "Non-Traditional *Acne* Therapy: The Use of Lasers and Light-Based Therapies," US Dermatology Review 2006, 4 pages, 2006.
Tremblay, J.F. et al., "Light-Emitting Diode 415 nm in the Treatment of Inflammatory *Acne*: An Open-Label, Multicentric, Pilot Investigation," Journal of Cosmetic and Laser Therapy, vol. 8, 3 pages, Jan. 25, 2006.
Goldberg, David J. et al., "Combination Blue (415 nm) and red (633 nm) LED Phototherapy in the Treatment of Mild to Severe *Acne vulgaris*," Jornal of Cosmetic and Laser Therapy, vol. 8, 5 pages, Mar. 29, 2006.
Lee, Seung Yoon et al., "Blue and Red Light Combination LED Phototherapy for *Acne vulgaris* in Patients with Skin Phototype IV," Lasers in Surgery and Medicine, vol. 39, 9 pages, Nov. 16, 2006.
Nestor, M., "The Use of Photodynamic Therapy for Treatment of *Acne vulgaris*," Dermatologic Clinics, vol. 25, 11 pages, 2007.
"Light Dose Ranging Study of Photodynamic Therapy (PDT) with Levulan + Blue Light in Severe Facial *Acne*," DUSA Pharmaceuticals, Inc., http://clinicaltrials.gov/ct2/show/NCT00706433, 25 pages, Mar. 2007.
Anonymous, "BlueLight *Acne* Treatments," [Online], Retrieved from Internet: http://www.topdocs.com/display_procedure.php?id—bluelight, 2 pages, Apr. 10, 2008.
"Comparison of Claro to Other Dermatological Devices for *Acne* Treatment," Quantitative Assessment of Light Illumination on Organism Reduction; Subculture agar: TSA + 5% Sheep's Blood (Blood agar) Organism Diluent: Butterfield's Buffer or 0.85% Saline; *Propionibacterium Acnes* (ATCC 11827), 16 pages, Jun. 23, 2008.
Anonymous, "Vi Derm Product Line," [Online], Kalil Medical Products, Retrieved from Internet: http://www.kalilmedical.com/doctor/vi_derm_products.asp, 4 pages, Mar. 2, 2010.
International Search Report, Application No. PCT/US2009/056961, 7 pages, Jun. 29, 2010.
International Preliminary Report on Patentability, PCT/US2009/056961, 11 pages, Mar. 22, 2011.
International Preliminary Report on Patentability, PCT/US2009/057204, 8 pages, Mar. 22, 2011.
Supplementary European Search Report, Application No. 09815144, 9 pages, Feb. 10, 2012.
European Office Action, Application No. 09815144.2, 6 pages, Oct. 10, 2012.
Japanese Office Action, Application No. 2010-520342, 6 pages, Mar. 7, 2013.
European Office Action, Application No. 09815144.2, 5 pages, Apr. 3, 2013.
Japanese Final Office Action, Application No. 2010-520342, 6 pages, Aug. 20, 2013.

\* cited by examiner

CAPACITIVE SENSING METHOD AND DEVICE FOR DETECTING SKIN

RELATED APPLICATIONS

This application claims the benefit of U.S. 60/954,682 filed Aug. 8, 2007. This application is a continuation-in-part of (a) U.S. Ser. No. 10/783,607, filed Feb. 19, 2004, issued as U.S. Pat. No. 7,118,563, which claims the benefit of U.S. Provisional Application Nos. 60/450,243, filed Feb. 25, 2003; 60/450,598, filed Feb. 26, 2003; 60/451,091, filed Feb. 28, 2003; 60/452,304, filed Mar. 4, 2003; 60/451,981, filed Mar. 4, 2003; 60/452,591, filed Mar. 6, 2003; 60/456,379, filed Mar. 20, 2003; 60/456,586, filed Mar. 21, 2003; 60/458,861, filed Mar. 27, 2003; and 60/472,056, filed May 20, 2003; (b) U.S. Ser. No. 11/545,963, filed Oct. 10, 2006, which is a continuation of (a) U.S. Ser. No. 10/783,607; (c) U.S. Ser. No. 10/783,603, filed Feb. 19, 2004, issued as U.S. Pat. No. 7,452,356; (d) U.S. Ser. No. 10/783,880, filed Feb. 19, 2004, issued as U.S. Pat. No. 7,250,045, (e) U.S. Ser. No. 10/787,720, filed Feb. 25, 2004, issued as U.S. Pat. No. 7,413,567; (f) U.S. Ser. No. 10/787,969, filed Feb. 25, 2004, issued as U.S. Pat. No. 7,981,111; (g) U.S. Ser. No. 10/788,167, filed Feb. 25, 2004; (h) U.S. Ser. No. 11/829,747, filed Jul. 27, 2007, and (i) U.S. Ser. No. 10/794,504, filed Mar. 5, 2004, all of which applications are incorporated herein by reference.

FIELD OF THE INVENTION

The present invention relates to devices and methods which involve skin contact sensors for dermatologic treatment, and more particularly relates to capacitive sensors in dermatologic devices for detecting the proximity of human skin.

BACKGROUND OF INVENTION

Many skin treatment devices require contact between an active area of the device and the skin for reasons of safety and/or efficacy.

For example, in light-based hair removal systems, the light energy is typically delivered through a transparent surface that makes contact with the skin. In such systems, the active area of the device is the light-emitting surface, and contact between this surface and the area of the skin to be treated is desirable both to ensure good transmission of the light to the treatment area, and, depending upon whether the device is otherwise eye safe, to aid in eye safety by eliminating stray light that might pose an eye hazard. At the same time, it is desirable to provide a system which does not require that the light-emitting surface be pressed into the skin to such a degree that the skin deforms.

Other examples of treatment devices that require skin contact include (1) devices that require contact only to prevent light leakage, such as a UV illuminator that requires no skin cooling but has a contacting baffle to prevent stray light, or (2) devices that require contact only for their mechanism of action and not to prevent light leakage, such as a thermal heater that delivers a pulse of heat through direct conduction to the skin. Other dermatological devices and methods that involve skin contact include ultrasound and radio frequency applications, such as wrinkle reduction. Some dermatological devices and methods provide skin contact through an interface material, such as ultrasound gel, oil, water, or index matching fluid. It is to be understood that these devices and methods are still considered to be skin contacting for the purposes of this application.

A significant problem for such devices is that the operator may angle or tilt the device's applicator such that it is not substantially perpendicular to the skin. This can create the situation where the entire surface of the active area is not in contact with the skin, and therefore the objective of efficacy and, for those devices which are not otherwise eye safe, will not be achieved.

Another problem for light-based devices is to ensure that the light-emitting surface is contacting a surface appropriate for treatment rather than, for example, eyeglasses. Typical contact sensors would generally sense positive contact if an applicator was applied to a person's eyeglasses, creating a potential for emission directly into the eye that, for many devices, could lead to serious injury or blindness. A similar condition could be created with household window panes or other similar transparent surfaces, whereby a contact sensor could sense contact against the window and light could be dangerously emitted into the ambient environment. It is desirable, therefore, for a dermatologic contact sensor not to be activated by eyeglasses or similar surfaces, but preferably only by a surface suitable for treatment.

A review of the state of the art shows that the existing devices and methods have important deficiencies. In particular, the existing designs do not solve the problem described above where the device applicator is applied at an angle and do not properly detect skin. While various mechanical systems exist which attempt to prevent dangerous emissions, most mechanical devices are complicated, costly and unreliable, as well as other shortcomings. A key advantage of capacitive sensing is its inherent imperviousness to ESD damage since no direct electrical connection to the skin is required. Although not necessary for capacitive sensing, it is possible to insulate the sensors of a capacitive sensor with a thin, electrically insulating, dielectric material.

Thus, there is a clear need for a practical contact sensor for skin treatment devices that would detect skin contact and also ensure skin contact across the entire active area of the device.

SUMMARY OF THE INVENTION

The foregoing and other problems and disadvantages of contact sensors in skin treatment devices are overcome by the present invention of a dermatologic treatment device comprising a capacitive skin sensing structure. The capacitive sensing structure permits activation of an associated treatment source only when skin is detected and the active area of the treatment source is properly in contact with the treatment area. In an embodiment, the capacitive sensing structure comprises a plurality of sensors, for example, three, positioned around the periphery of the treatment area. Each sensor is a planar metal region that forms one electrode of a parallel plate capacitor, the second electrode being formed by a corresponding region of the skin. By properly arranging the sensors around the active area, when the capacitive sensing structure contacts skin, the user can be assured that the active area of the treatment device is also in contact with skin, even though no deformation of the skin is necessary. The juxtaposition of skin against the sensing structure causes the capacitance of the sensing structure to change with an identifiable characteristic such that associated control circuitry can detect the difference. Once that change is capacitance is detected, the control circuitry permits the treatment source to be activated. At the same time, juxtaposition of other materials against the surface does not properly change the capacitance of the sensor, and the associated control circuitry will not permit the treatment source to be activated.

In one embodiment the treatment source includes a source of electromagnetic radiation, and the active area of the treatment source comprises a window through which electromagnetic radiation is emitted. The source of electromagnetic radiation and the dermatologic treatment can be configured to provide hair regrowth inhibition. In such an embodiment, activation of the source of magnetic radiation will be inhibited unless contact with skin is sensed by way of the sensors, without requiring deformation of the skin.

Other embodiments of the dermatologic treatment device are contemplated in which the treatment source is a source of electromagnetic radiation which is configured for such treatments as acne treatment, photorejuvenation, wrinkle reduction, depigmentation, or repigmentation, and the activation of the source of magnetic radiation is inhibited unless contact with skin is sensed by way of the capacitive sensing structure.

In further embodiments of the present invention, the active area of the treatment device is surrounded by a bezel which forms a substantially planar surface with the active area. The capacitive sensors are maintained behind the bezel but in sufficiently close proximity to it that they can sense the presence of skin. The substantially planar surface ensures good contact between the active area and the skin without deformation of the skin. In other embodiments, the active area can be placed forward of the bezel surface, and the sensitivity of the capacitive sensor structure can be configured to permit activation of the treatment source without deformation of the skin. In still other embodiments, the active area can be placed sufficiently forward of the skin sensing structure that deformation of the skin is required before the capacitive sensor will permit activation of the treatment source. In other embodiments, the number of skin contacting sensors is varied from one to six or more.

Other embodiments comprise a capacitive skin sensor that is activated when the active area is merely in close proximity to the skin, and can be used for procedures in which any contact with the skin is undesirable. In yet another embodiment of the present invention, the sensors are merely small conductive contact areas, for example on the order of one millimeter in diameter. Each of the sensors are electrically connected to an associated, remotely located fixed capacitor. In an embodiment, one capacitor is associated with each contact area, although this one-to-one correspondence is not necessarily used in every such embodiment.

In accordance with the present invention, a method for providing a skin contact sensor in a dermatologic treatment device having a skin contacting structure and a treatment source capable of being activated to supply a dermatologic treatment through the skin contacting structure, includes the steps of positioning a plurality of capacitive sensors around a periphery of the active area of a treatment source, and inhibiting activation of the treatment source unless the present of skin is indicated by signals from the plurality of sensors. The method can further include the step of configuring the active area together with the plurality of sensors so that no deformation of the skin is required, and can, alternatively, include the step of configuring the active area relative to the sensors so that deformation of the skin is required.

It is therefore an object of the present invention to provide a skin contact sensor and method suitable for use in dermatologic treatment devices.

It is another object of the present invention to provide a skin contact sensor and method for dermatologic treatment devices in which the skin contact sensor inhibits activation of a treatment source in the device unless contact with a compliant surface is sensed.

It is a further object of the present invention to provide a dermatologic treatment device having a skin contact sensor including a plurality of sensors positioned around a periphery of a skin contacting structure and circuitry coupled to the plurality of sensors and configured to inhibit activation of a treatment source in the device other than in the presence of skin.

It is still another object of the present invention to provide a skin contact sensor and method for use in dermatologic treatment devices in which a plurality of sensors are positioned around a treatment window and the plurality of sensors are positioned relative to a skin contacting surface such that no deformation of skin is required during use of the treatment device.

It is a still further object of the present invention to provide a skin contact sensor configuration and method in a dermatologic treatment device in which a three or more sensors are positioned around a treatment window and a skin-contacting surface of the treatment window is substantially coplanar with a bezel.

These and other objectives, advantages and features of the present invention will be more readily understood upon considering the following detailed description of certain preferred embodiments of the present invention, and the accompanying drawings.

Attention is drawn to the aforementioned Related Applications. It will be appreciated by those skilled in the art that aspects and features disclosed in those applications may be configured so as to be suitable for use with the contact sensor device and method described herein.

DETAILED DESCRIPTION OF THE INVENTION

Figure 1:
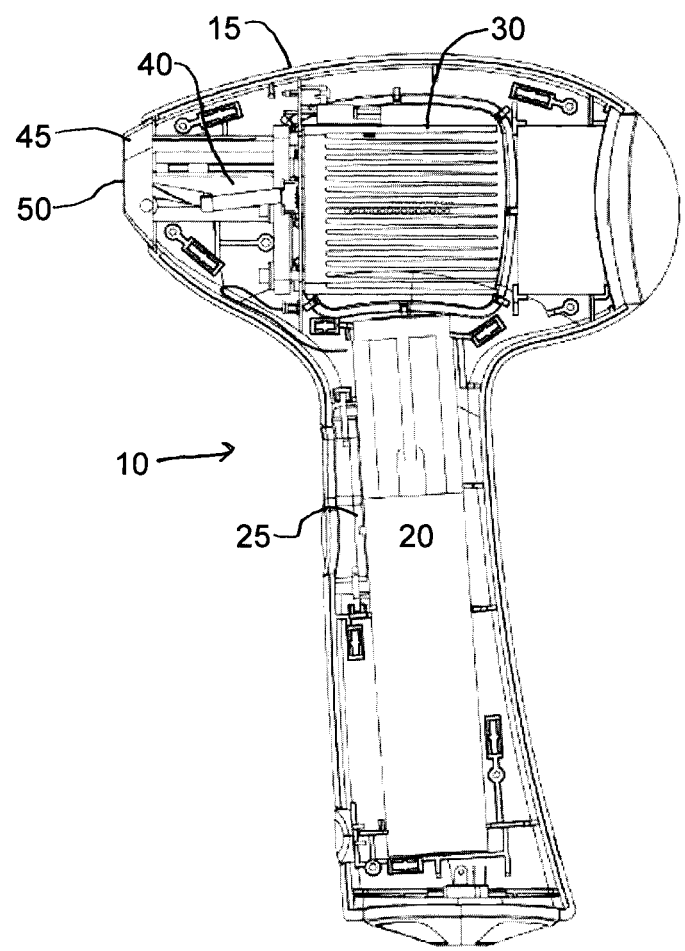
FIG. 1 illustrates in side elevational view one example of a treatment device such as might be used in connection with the present invention.
Figure 2:
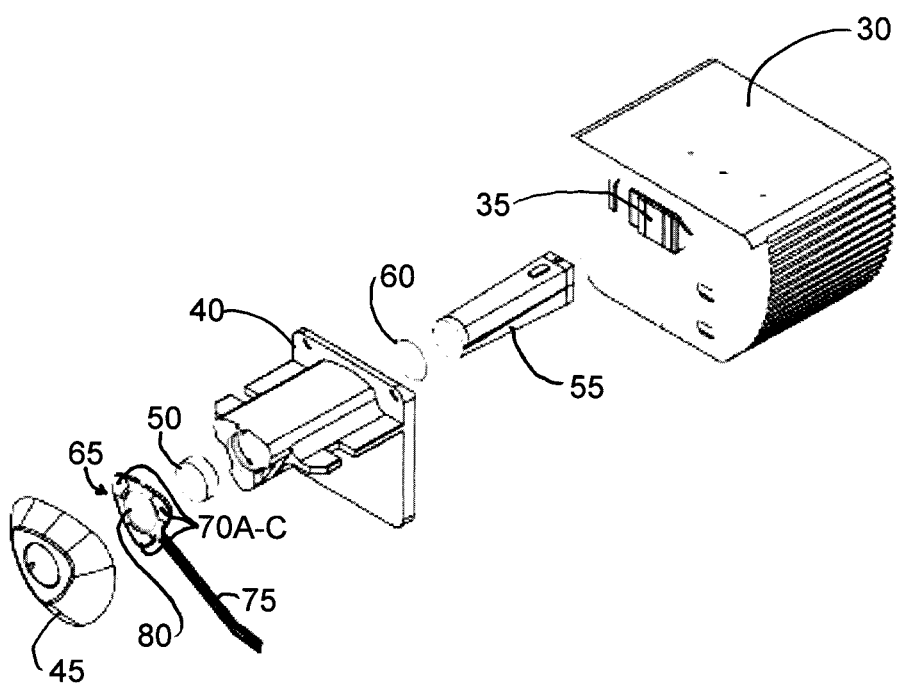
FIG. 2 is an exploded perspective view of a portion of the device of FIG. 1, showing an embodiment of a treatment source together with a capacitive skin sensor structure.

Referring first to FIGS. 1 and 2, FIG. 1 shows a dermatologic treatment device such as might be used with the present invention. FIG. 2 shows a more detailed view of a treatment source and a capacitive skin sensor intended to be integrated therewith. In typical embodiments, although not necessarily in every embodiment, the present invention is integrated into the treatment device. For purposes of clarity, such an integrated device is illustrated in the Figures and will be described hereinafter. In addition, while the device shown in the Figures and discussed hereinafter uses light for the purpose of hair removal or reduction, it will be appreciated that this arrangement is merely exemplary, and devices utilizing the present invention can include acne treatment devices, repigmentation devices, and so on, and can use different types of treatment sources including radiation of other wavelengths. Further, while the device shown in FIG. 1 is hand held, self contained and portable, it will be appreciated that the present invention is not so limited and can be used with devices having none or only some of these features.

In the device of FIG. 1, a treatment device 10 includes a housing 15, a battery 20, control circuitry 25, a heat sink 30 on which are mounted a treatment source 35 (FIG. 2) which can, for example, comprise one or more laser diodes 35A of a wavelength suited to the particular type of treatment, and a barrel 40 affixed to the front of the heat sink and aligned with the treatment source. A bezel 45 encloses an active area better seen in FIG. 2, which can, for example, comprise a window 50 in optical communication with the treatment source 35. For the illustrated embodiment, a mixer 55 and diffuser 60 are maintained within the barrel 40. For the particular design shown, the diffuser, treatment source, and remaining components are configured to be eye safe with regard to retinal damage, although the present invention is not limited to such eye safe configurations.

Figure 3:
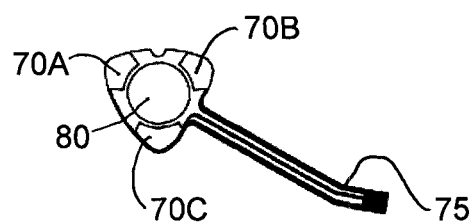
FIG. 3 shows the capacitive sensing structure of FIGS. 1-4, including the associated ribbon cable.

In addition, and as shown particularly in FIGS. 2 and 3, a capacitive sensing structure 65 is positioned at the front of the barrel, and includes an orifice 80 configured to substantially surround the window 50. For the embodiment illustrated, the capacitive sensing structure 65 comprises three capacitive sensors 70A-C positioned substantially equilaterally around the window 50, although other embodiments can have one or more sensors, and the sensors need not be positioned at equal angles around the periphery of the window 50. A ribbon cable 75, or pigtail, connects the sensors 70A-C to control circuitry 85, best seen in FIGS. 4 and 5. The relationship between the window 50, the orifice 80 and the remainder of the capacitive sensing structure 65 can be better appreciated from the perspective view of FIG. 4.

To prevent artifact signals from occurring, the ribbon cable 75, for some embodiments, comprises a polyimide base layer and polyimide coverlay of sufficient thickness to prevent contaminants from being deposited in close proximity to the inner conductive traces. In some embodiments, polyimide thickness in the range of one to ten or more one-thousandths of an inch can be used if necessary to provide a sufficient insulation layer to prevent the ribbon cable from providing sufficient stray capacitance to affect the operation of the sensors 70A-C.

Figure 5:
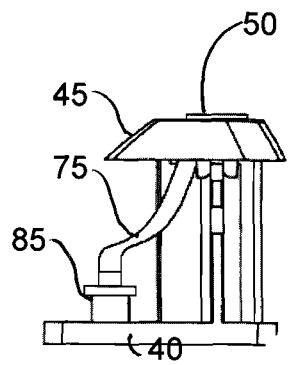
FIG. 5 is a side view of the subassembly of FIG. 3, showing a ribbon cable connecting the capacitive sensor structure to control circuitry.
Figure 4:
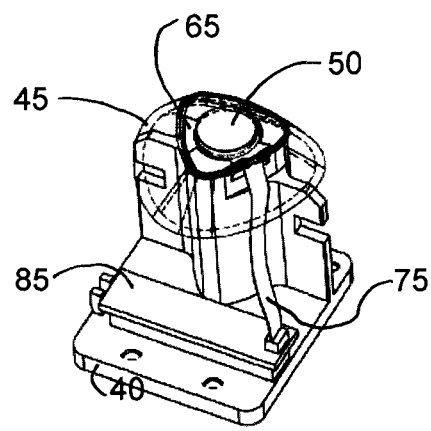
FIG. 4 is a perspective view of the barrel and associated components shown in FIG. 2, including the capacitive sensor structure and active area of the treatment device.

From FIGS. 4 and 5, it can also be appreciated that the bezel 45 is substantially coplanar with the window 50, such that the combination of the bezel and window provide a flat surface that permits operation of the device with no deformation of the skin in the target area. However, in alternative embodiments the relative positioning of the sensors 70A-C and the window 50, together with the shape of the bezel 45, can be adjusted such that the device will operate without deformation of the skin even though the bezel and window are not co-planar. Similarly, the relative arrangement can also be configured to require deformation of the skin to permit the treatment source to be activated. Further, in some embodiments, such as where skin contact is not desirable, the sensors 70A-C can be positioned to operate as proximity sensors, so that the device will operate without contact between the bezel 45 and the skin. In the embodiment shown in FIGS. 1-5, the bezel 45 is typically positioned such that the sensors 70A-C contact the back of the bezel, although this need not be the case in all embodiments. In the embodiment shown, the bezel, or at least the tip portion of the bezel positioned over the sensors 70A-C, can be made from polycarbonate, for example Panlite L-1225L, with a nominal thickness 0.015"+/−0.002", and a dielectric constant on the order of 2.95. Alternatively, the tip portion can be made from, among other materials, a polycarbonate/ABS (Acrylonitrile Butadiene Styrene) blend such as GE Cycoloy C6200, with a dielectric constant of 2.8. As a further alternative, the tip portion can be made from ABS such as Cycolac GPM550, with a dielectric constant of 2.7, or an acrylic material such as Sumipex, having a dielectric constant of 3.3. However, some acrylic materials are brittle, which may be undesirable in at least some embodiments. A still further alternative is acetal, such as Delrin 900P, with a dielectric constant of 3.8.

Figure 6:
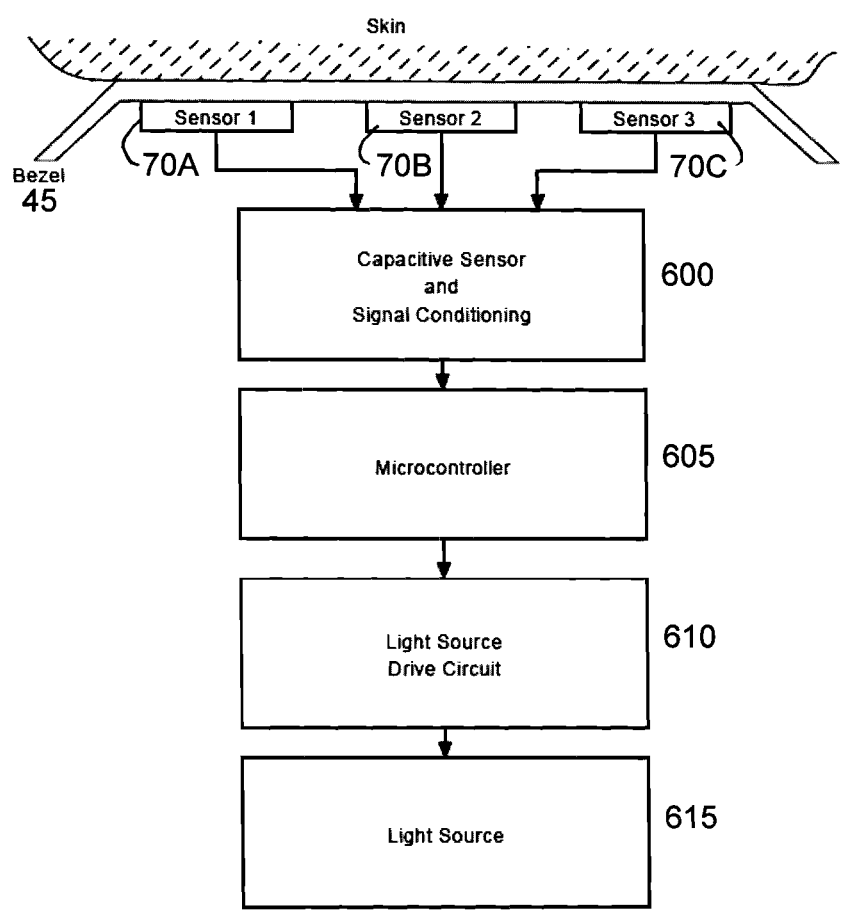
FIG. 6 is a schematic block diagram showing the operation of the capacitive sensing structure in combination with the control circuitry to permit the light source, or treatment source, to be activated.

Referring next to FIG. 6, the electrical circuit comprising the capacitive sensors and associated control circuitry can be better appreciated. The sensors 70A-C each provide a signal to a capacitive sensor and signal conditioning circuit 600, which detects variations in the capacitance of the sensors and, depending upon the threshold set in the circuit 600, notifies microcontroller 605 that skin has been detected. It will be appreciated by those skilled in the art that the sensors 70A-C are, in at least some embodiments, sensed by grounding two terminals of the sensor and detecting variations in the rate of charge or discharge measured at the third terminal. In addition, it will be appreciated that the sensors may be sensed sequentially or all at once, depending upon the configuration, although in a presently preferred arrangement the sensors are sensed sequentially. In an embodiment, the capacitive sensor structure 600 is a customized MC9S08QD4CSC microcontroller from Freescale, and the microcontroller circuit 605 is a P18LF452-I/PT, from Microchip. However, although the circuit 600 has been shown separately from the microcontroller (and associated circuitry) 605 in FIG. 6, those skilled in the art will recognize that the functions of the circuit 600 can be performed in the microcontroller 605, and thus in many embodiments the circuit 600 and microcontroller 605 will be integrated as a single unit. The microcontroller 605 in turns provides control signals to a light source circuit 610, which provides power to the light source 615.

For the treatment device shown in FIG. 1, in an embodiment it is preferred that skin be detected at each of the sensors 70A-C before the microcontroller 605 will activate the treatment source, or light source, 35. However, it will also be appreciated that, for some embodiments, it is not necessary to have all three detectors sense skin, in which case the microcontroller is programmed to operate in response to detection of skin at the appropriate number of sensors.

Figure 7:
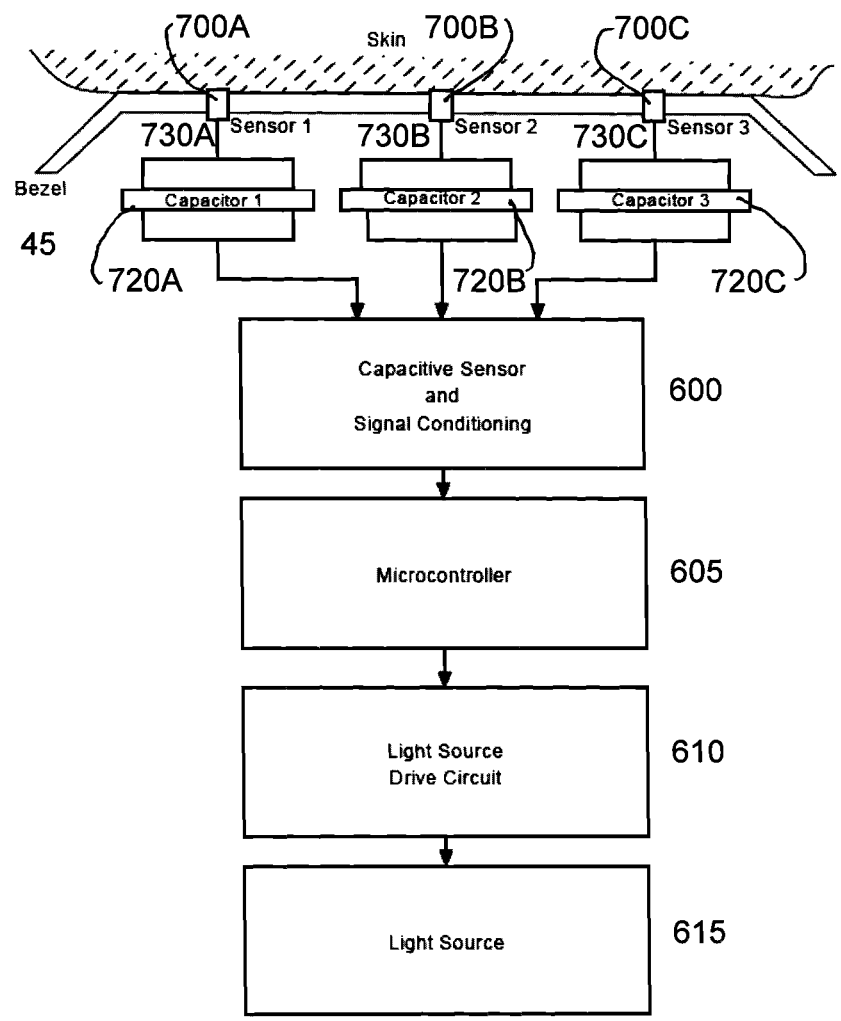
FIG. 7 is a schematic block diagram showing the operation of the capacitive sensing structure that incorporates remote capacitors and smaller skin sensors.

FIG. 7 shows an alternative embodiment of the sensors where the pads 70A-C of FIG. 1 are replaced with small sensors 700A-C that extend through the bezel 710 and electrically connect to remote fixed capacitors 720A-C by means of conductors 730A-C. The small sensors 700A-C are metal in an embodiment but in other embodiments can be other types of low impedance conductive material. This embodiment allows for a smaller overall capacitive sensing structure while maintaining ESD imperviousness as provided by the insulating dielectric material in the remote fixed capacitors. The smaller sensors 700A-C of this embodiment do not need to make electrical contact with the skin. Instead, it is likely that, in at least some embodiments, an oxide layer or other incidental film on the sensors 700A-C, or a layer of dead or dehydrated skin will entirely or partially insulate the sensor 700A-C from the skin. Even if a sufficiently low resistive contact is not made between the skin and the sensor 700A-C, an effectively large capacitance between the sensor 700A-C and the skin will be present due to the relatively thin incidental film between the sensor 700A-C and skin (as compared to a configuration with a thicker structure arranged between the sensors and the skin). As shown in FIG. 7, this relatively large capacitance will be in series with the larger remote fixed capacitors 720A-C such that the larger capacitance of the remote fixed capacitors 720A-C will not effect the measurement of the capacitance between the sensors 700A-C and the skin. An additional feature of this arrangement is that the dielectric constant of the remote capacitors 720A-C can be adjusted to provide the desired sensitivity for the detection of the proximity of skin to the sensors 700A-C. As can be appreciated from FIG. 7, the remaining functions shown in FIG. 7 are substantially identical, on a functional level, to the same functions in FIG. 6, and so like elements are given like reference numerals. The ability to place the place the capacitors 720A-C somewhat remotely from surface of the bezel permits larger capacitors to be used, which can provide increased sensitivity of changes in the capacitance between the sensors 700A-C and the skin. This arrangement also allows designs that protect against electrostatic discharge, because the remote placement of the capacitors allows the use of capacitors that have sufficient distance between the terminals to prevent arcing from one terminal to the other.

Figure 8:
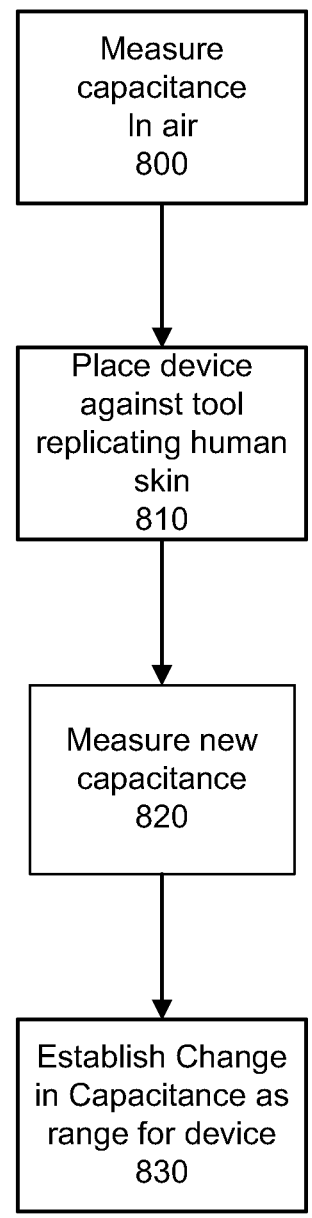
FIG. 8 is a flow diagram illustrating a calibration process used with some embodiments of the invention.

In some embodiments, it is desirable to calibrate the sensors since the sensitivity of the sensors can vary somewhat from device to device. This calibration can be achieved during manufacturing as shown in FIG. 8. At step 800, a baseline capacitance in open air is measured. Then using a tool which replicates human skin with known and repeatable characteristics, at 810 the sensors are placed against the tool. This yields a change in capacitance, as measured at 820. The change in capacitance between open air and direct contact with skin provides a range, which can then be used as shown at 830 to establish the characteristics of that specific sensor.

It will be appreciated by those skilled in the art that numerous alternatives and equivalents can be implemented without deviating from the invention. As some examples, various sensor geometries can be used, including varying the number of sensors, the effective size of the sensors, the distance the sensor is recessed from the active skin-contacting surface of the device, and other such configurations. In an embodiment of the present invention, such as that illustrated in the Figures, the active area of each sensor 70 is less on the order of 0.200"×0.150" [dimensions].

Likewise, other types of sensor circuitry can be used. The sensor output can be processed purely in hardware, or the device can employ a variety of different software and/or hardware algorithms to change safety, reliability, or effectiveness characteristics, such as allowing use if three of four buttons indicated contact. Additionally, the circuitry can compare signals from the sensors for various additional purposes, such as to estimate the total heat flux through the contact surface.

It will therefore be appreciated that, while exemplary drawings and specific embodiments of the present invention have been described and illustrated, the scope of the present invention is not be limited to the particular embodiments discussed. The embodiments shown and described are to be regarded as illustrative rather than restrictive, and the invention is to be limited only by the appended claims.

In addition, in methods that may be performed according to preferred embodiments herein and that may have been described above, the operations have been described in selected sequences. However, the sequences have been selected and so ordered for solely for clarity and convenience and are not intended to imply a requirement for any particular order for performing the operations, unless expressly set forth in the claims or as understood by those skilled in the art as being necessary.

We claim:

1. A dermatologic treatment device comprising:
a light source having an output,
a window at an output end of the device for emitting light from the light source,
a bezel surrounding the window and having a thickness,
a plurality of low impedance conductive contacts arranged around the periphery of the window at the output end of the device, each low impedance conductive contact having a physical structure extending through the thickness of the bezel and defining a conductive outer surface configured for physical contact with a person's skin,
a plurality of capacitors, each capacitor electrically connected to one of the contacts and arranged spaced apart from the output end of the device, and
a controller responsive to a perceived change in the value of at least one of the capacitors resulting from the presence of skin at the associated contacts, such that the light source emits light only when the presence of skin is detected by the controller.

2. The dermatologic treatment device of claim 1 wherein the bezel is plastic.

3. The dermatologic treatment device of claim 1 wherein the number of contacts is at least three.

4. The dermatologic treatment device of claim 3 wherein the light source emits light only when the change in at least three of the capacitors indicates the presence of skin.

5. The dermatologic treatment device of claim 1 wherein the light source emits light only when the change in at least two of the capacitors indicates the presence of skin.

6. The dermatologic treatment device of claim 1 wherein the window and the bezel are substantially coplanar.

7. A skin detection apparatus comprising:
an electrically non-conducting surface,
at least one electrically conductive sensor arranged in or projecting forward from the surface and configured to be placed proximate to the skin, thereby creating a capacitance between each sensor and the skin,
a capacitive sensor circuit electrically coupled to the at least one sensor, and
at least one capacitor electrically connected in series between the at least one sensor and the capacitive sensor circuit and arranged spaced apart from the at least one sensor,
wherein the capacitive sensor circuit is configured to detect changes in capacitance between the at least one sensor and the skin when the at least one sensor is proximate to the skin,
wherein the at least one capacitor connected in series between the sensor and the capacitive sensor circuit and arranged spaced apart from the at least one sensor is configured to protect against electrostatic discharge, while allowing the capacitive sensor circuit to detect changes in capacitance between the at least one sensor and the skin, and
a controller connected to the capacitive sensor circuit and configured to generate an output signal indicative of the presence of skin based on signals from the capacitive sensor circuit.

8. The skin detection apparatus of claim 7 wherein the number of capacitors is at least three.

9. The skin detection apparatus of claim 8 wherein the electrically non-conducting surface has an aperture therethrough.

10. The skin detection apparatus of claim 9 wherein the aperture is configured to permit the emission of light therethrough.

11. The skin detection apparatus of claim 7 wherein the surface has an aperture therethrough, and the controller enables a light source to emit light through the aperture when the presence of skin is detected.

12. The skin detection apparatus of claim 7 wherein no physical contact between skin and the at least one electrically conductive sensor is required for the controller to detect the presence of skin.

\* \* \* \* \*